(12) United States Patent
Naitoh

(10) Patent No.: US 8,294,121 B2
(45) Date of Patent: Oct. 23, 2012

(54) FIXING INSTRUMENT

(75) Inventor: Shigeaki Naitoh, Gunma (JP)

(73) Assignee: Advantest Corporation, Tokyo (JP)

( * ) Notice: Subject to any disclaimer, the term of this patent is extended or adjusted under 35 U.S.C. 154(b) by 88 days.

(21) Appl. No.: 12/647,690

(22) Filed: Dec. 28, 2009

(65) Prior Publication Data

US 2011/0108740 A1    May 12, 2011

(30) Foreign Application Priority Data

Nov. 10, 2009   (JP) ................. 2009-257044

(51) Int. Cl.
*G01N 21/64* (2006.01)

(52) U.S. Cl. ................. 250/453.11; 257/99; 324/754.23

(58) Field of Classification Search ............. 250/453.11
See application file for complete search history.

(56) References Cited

U.S. PATENT DOCUMENTS

| | | | |
|---|---|---|---|
| 7,119,339 B2 | 10/2006 | Ferguson et al. | |
| 7,755,100 B2 * | 7/2010 | Choi et al. | 257/99 |
| 2010/0271056 A1 * | 10/2010 | Irisawa et al. | 324/750 |

FOREIGN PATENT DOCUMENTS

| | | |
|---|---|---|
| JP | 63-285126 | 11/1988 |
| JP | 4-8952 | 1/1992 |
| JP | 8-304229 | 11/1996 |
| JP | 2001-021448 | 1/2001 |
| JP | 2007-229320 | 9/2007 |

OTHER PUBLICATIONS

S. Wang et el., "Pulsed terahertz tomography," J. Phys. D: Appl. Phys., vol. 37, R1-R36, 2004.
U.S. Appl. No. 12/486,178 to Irisawa et al., which was filed on Jun. 17, 2009.
U.S. Appl. No. 12/617,129 to Nishina et al., which was filed on Nov. 12, 2009.
Search report in PCT/JP2010/070157, mail date is Jan. 18, 2011.

* cited by examiner

*Primary Examiner* — Phillip A Johnston
(74) *Attorney, Agent, or Firm* — Greenblum & Bernstein P.L.C.

(57) ABSTRACT

Fixtures according to the present invention include fixing surfaces in the same shape as end surfaces of a device under test which is to be measured while an electromagnetic wave to be measured at a frequency equal to more than 0.01 [THz] and equal to or less than 100 [THz] is irradiated on the device under test. The end surfaces are fixed to the fixing surfaces. When a refractive index of the fixtures is n0, and a refractive index of the device under test is n1, a relationship $n1-0.1 \leq n0 \leq n1+0.1$ holds. The fixtures do not cover a side surface of the device under test. The fixtures are rotated about a straight line orthogonal to the fixing surfaces as a rotational axis.

13 Claims, 20 Drawing Sheets

$n1 > n2$
$\theta_A > \theta_B$ $1 < n1 < n2$

Comparative Example (Fixture 100a is not present)

Comparative Example (Side Surface 1e is covered)

FIXING INSTRUMENT

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been the computed tomography (CT) as a method for obtaining tomographic information on a device under test. This method conducted while a generator and a detector of the X ray are used is referred to as X-ray CT. With the X-ray CT, it is possible to acquire tomographic information on a human body in non-destructive and non-contact manner.

However, it is difficult for the X-ray CT to detect internal states (such as defects and distortions) of industrial products constructed by semiconductors, plastics, ceramics, woods, and papers (referred to as "raw materials" hereinafter). This is because the X-ray presents a high transmission property to any materials.

On the other hand, the terahertz wave properly transmits through the raw materials of the industrial products described above. Therefore, the CT carried out while a generator and a detector of the terahertz wave are used (referred to as "terahertz CT" hereinafter) can detect internal states of the industrial products. Patent Document 1 and Non-Patent Document 1 describe the terahertz CT.

(Patent Document 1) U.S. Pat. No. 7,119,339
(Non-Patent Document 1) S. Wang et al., "Pulsed terahertz tomography," J. Phys. D, Vol. 37 (2004), R1-R36

SUMMARY OF THE INVENTION

However, according to the terahertz CT, when the terahertz wave is obliquely made incident to or emitted from a device under test, the terahertz wave is refracted, and thus does not travel straight. On this occasion, it is assumed that the refractive index of the ambient air of the device under test is 1, and the refractive index of the device under test for the terahertz CT is more than 1.

FIG. 20 shows estimated optical paths of the terahertz wave when the refractive index of a conventional device under test is 1.4, and the refractive index of the ambient air of the device under test is 1. Referring to FIG. 20, it is appreciated that terahertz wave made incident from the left of the device under test (DUT) is refracted by the DUT.

Due to the fact that the terahertz wave does not travel straight, the terahertz wave cannot reach a detector, and an image of the DUT cannot thus be obtained at a sufficient sensitivity.

Moreover, due to the fact that the terahertz wave does not travel straight, a detected terahertz wave may not have traveled straight through the DUT before the arrival. Therefore, when an image of the device under test is obtained from the detected terahertz wave, artifacts such as obstructive shadows and pseudo images may appear on the image.

Therefore, it is an object of the present invention, when an electromagnetic wave (frequency thereof is equal to or more than 0.01 [THz] and equal to or less than 100 [THz]) including the terahertz wave is fed to a DUT for measurement, to provide a fixture for the DUT which can be used along with a container for storing the DUT in order to restrain an adverse effect caused by a refraction of the electromagnetic wave including the terahertz wave by the DUT.

According to the present invention, a fixture includes a fixing surface in the same shape as an end surface of a device under test which is measured by irradiating an electromagnetic wave to be measured having a frequency equal to or more than 0.01 [THz] and equal to or less than 100 [THz] on the device under test, wherein: the end surface is fixed to the fixing surface; a relationship $n1-0.1 \leq n0 \leq n1+0.1$ holds, where $n0$ denotes a refractive index of the fixture and $n1$ denotes a refractive index of the device under test; and the fixture does not cover a side surface of the device under test.

According to the thus constructed fixture including a fixing surface in the same shape as an end surface of a device under test which is measured by irradiating an electromagnetic wave to be measured having a frequency equal to or more than 0.01 [THz] and equal to or less than 100 [THz] on the device under test, the end surface is fixed to the fixing surface. A relationship $n1-0.1 \leq n0 \leq n1+0.1$ holds, where $n0$ denotes a refractive index of the fixture and $n1$ denotes a refractive index of the device under test. The fixture does not cover a side surface of the device under test.

According to the present invention, the fixture may be rotated about a straight line orthogonal to the fixing surface as an axis.

According to the fixture of the present invention, a travel direction of the electromagnetic wave to be measured may be orthogonal to the straight line.

According to the fixture of the present invention, the end surface may be fixed to the fixing surface by pressing the fixing surface against the end surface.

According to the fixture of the present invention, there may be two of the fixtures; the device under test may have two of the end surfaces parallel with each other; and the two fixtures may be respectively pressed against the two end surfaces.

According to the fixture of the present invention, the end surface may be fixed to the fixing surface by adhering the fixing surface to the end surface.

According to the fixture of the present invention, at least a part of the device under test may be stored in a container; the container may include: a gap portion which internally disposes at least a part of the device under test, and an enclosure portion which includes a first curved surface portion and a second curved surface portion, and disposes the gap portion between the first curved surface portion and the second curved surface portion, thereby enclosing the gap portion; a refractive index $n2$ of the enclosure portion may be larger than a refractive index $n1$ of the device under test; and both the first curved surface portion and the second curved surface portion may be convex surfaces.

According to the fixture of the present invention, at least a part of the device under test may be stored in a container; the container may include: a gap portion which internally disposes at least a part of the device under test, and an enclosure portion which includes a first curved surface portion and a second curved surface portion, and disposes the gap portion between the first curved surface portion and the second curved surface portion, thereby enclosing the gap portion; the refractive index $n2$ of the enclosure portion may be smaller than the refractive index $n1$ of the device under test; and both the first curved surface portion and the second curved surface portion may be concave surfaces.

According to the fixture of the present invention, a contour of a plane shape of the gap portion of the container may include an arc.

According to the fixture of the present invention, at least a part of the device under test may be stored in a container; the container may include: a first cover portion including a first curved surface portion which receives the electromagnetic wave to be measured, and a first concave surface portion which is closer than the first curved surface portion to the device under test, and through which the electromagnetic wave to be measured transmits, and having a refractive index of n2a, and a second cover portion including a second concave surface portion which receives the electromagnetic wave to be measured which has transmitted through the device under test, and a second curved surface portion which is farther than the second concave surface portion from the device under test, and through which the electromagnetic wave to be measured transmits, and having a refraction index of n2b; and when a refractive index of the device under test is n1, if n2a is larger than n1, the first curved surface portion may be a convex surface, if n2a is smaller than n1, the first curved surface portion may be a concave surface, if n2b is larger than n1, the second curved surface portion may be a convex surface, and if n2b is smaller than n1, the second curved surface portion may be a concave surface.

According to the fixture of the present invention, n2a and n2b of the container may be different from each other.

According to the fixture of the present invention, a curvature radius of a plane shape of the first curved surface portion of the container and a curvature radius of a plane shape of the second curved surface portion of the container may be different from each other.

According to the fixture of the present invention, contours of plane shapes of the first concave surface portion and the second concave surface portion of the container may include an arc.

BRIEF DESCRIPTION OF THE DRAWINGS

FIGS. 1(a) to 1(c) are views of a container 10 according to a first embodiment of the present invention, in which FIG. 1(a) is a plan view, FIG. 1(b) is a left side view, and FIG. 1(c) is a right side view;

FIGS. 5(a) to 5(c) are views of the container 10 according to the second embodiment of the present invention, in which FIG. 5(a) is a plan view, FIG. 5(b) is a left side view, and FIG. 5(c) is a right side view;

FIGS. 11(a) to 11(d) are views of the fixtures 100a and the DUT 1, in which FIG. 11(a) is a front view of the fixture 100a, FIG. 11(b) is a bottom view of the fixture 100a, FIG. 11(c) is a plan view of the DUT 1, and FIG. 11(d) is a front view of the DUT 1;

FIGS. 12(a) to 12(d) are views of the DUT 1 and fixtures 100b, in which FIG. 12(a) is a front view of the DUT 1, FIG. 12(b) is a bottom view of the DUT 1, FIG. 11(c) is a plan view of the fixture 100b, and FIG. 12(d) is a front view of the fixture 100b;

BEST MODE FOR CARRYING OUT THE INVENTION

A description will now be given of embodiments of the present invention with reference to drawings.

First Embodiment

FIGS. 1(a) to 1(c) are views of a container 10 according to a first embodiment of the present invention, in which FIG. 1(a) is a plan view, FIG. 1(b) is a left side view, and FIG. 1(c) is a right side view. FIG. 2 is a plan view of a state in which at least a part of a device under test (DUT) 1 is stored in the container 10 according to the first embodiment of the present invention, and a terahertz wave is irradiated on the container 10.

Referring to FIG. 2, a terahertz wave measurement device (electromagnetic wave measurement device) includes a terahertz wave output device 2 and a terahertz wave detector 4. The terahertz wave output device 2 outputs the terahertz wave toward the DUT 1. The terahertz wave detector 4 detects the terahertz wave which has transmitted through the DUT 1 and the container 10.

It should be noted that the terahertz wave measurement device (electromagnetic wave measurement device) employs, as an electromagnetic wave to be measured, which is to be output and to be detected, the terahertz wave (the frequency thereof is equal to or more than 0.03 [THz] and equal to or less than 10 [THz], for example). However, the electromagnetic wave to be measured, which is to be output and detected by the terahertz wave measurement device (electromagnetic wave measurement device), is not limited to the terahertz wave, and may be an electromagnetic wave the frequency of which is equal to or more than 0.01 [THz] and equal to or less than 100 [THz].

The DUT 1 is measured by irradiating the electromagnetic wave to be measured thereupon.

Figure 10:
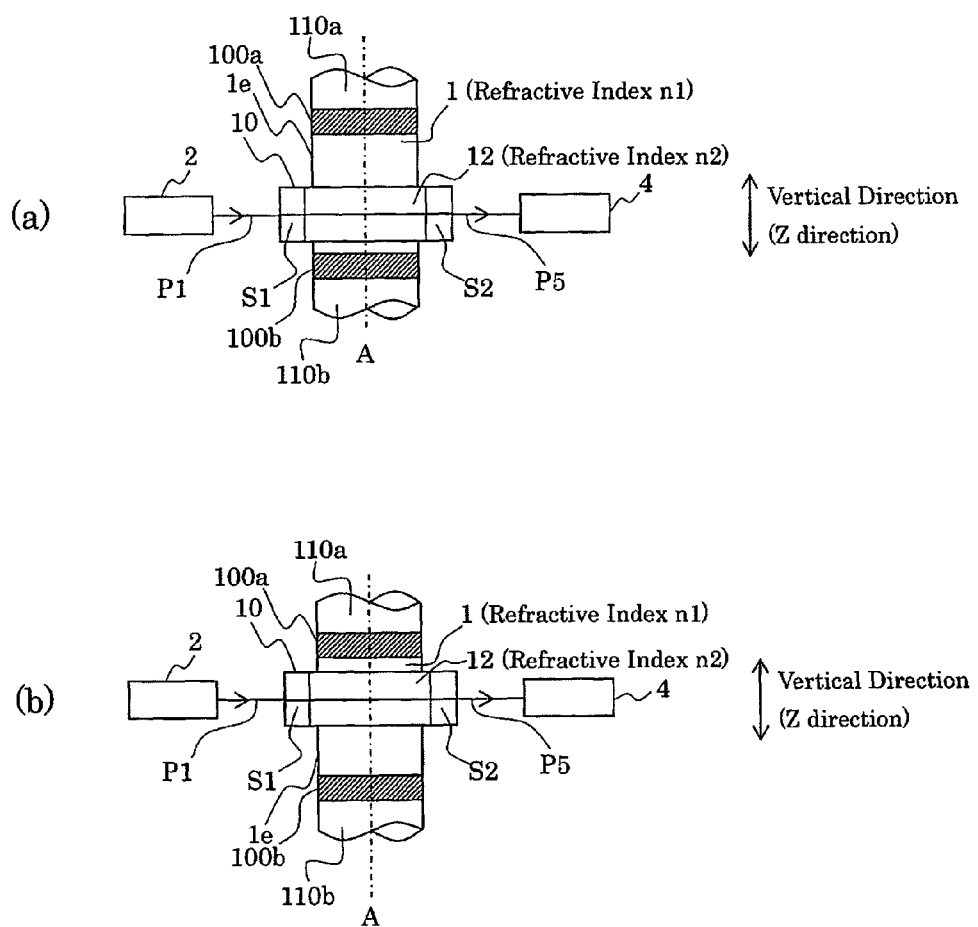
FIGS. 10(a) and 10(b) are front views of the container 10, the fixtures 100a and 100b, rotary actuators 110a and 110b, and the terahertz wave measurement device according to the fourth embodiment.
Figure 11:
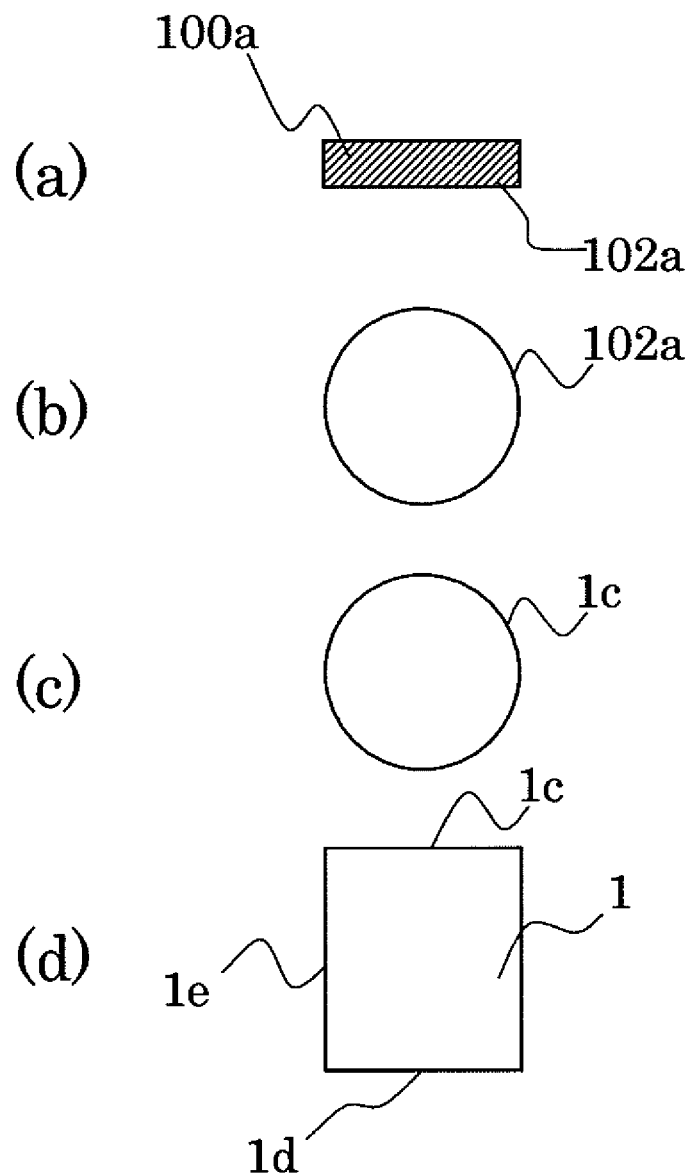
Figure 12:
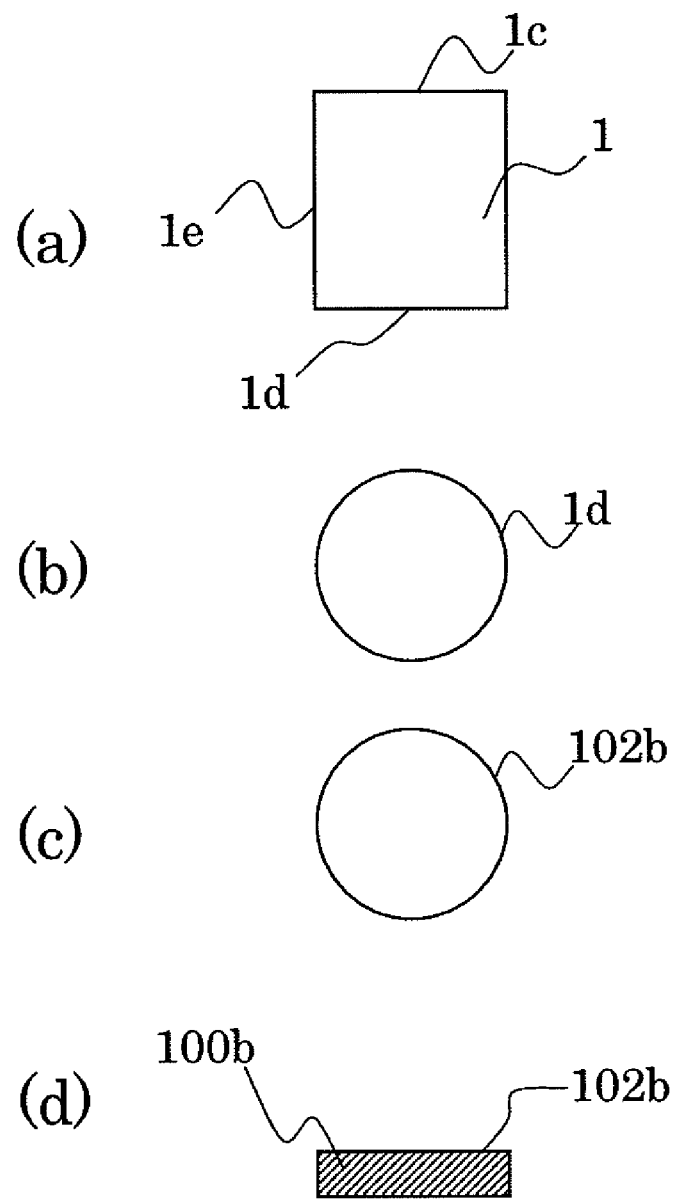
Figure 13:
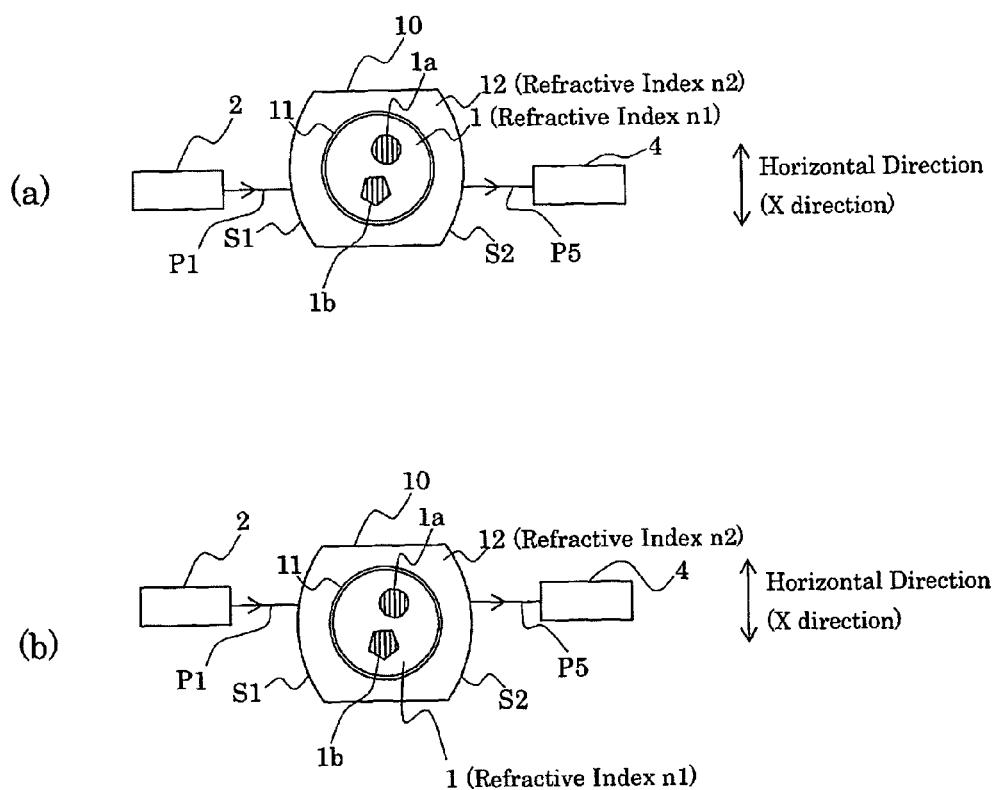
FIGS. 13(a) and 13(b) are plan views of the container 10 and the terahertz wave measurement device when the container 10 and the DUT 1 are moved in the X direction.
Figure 14:
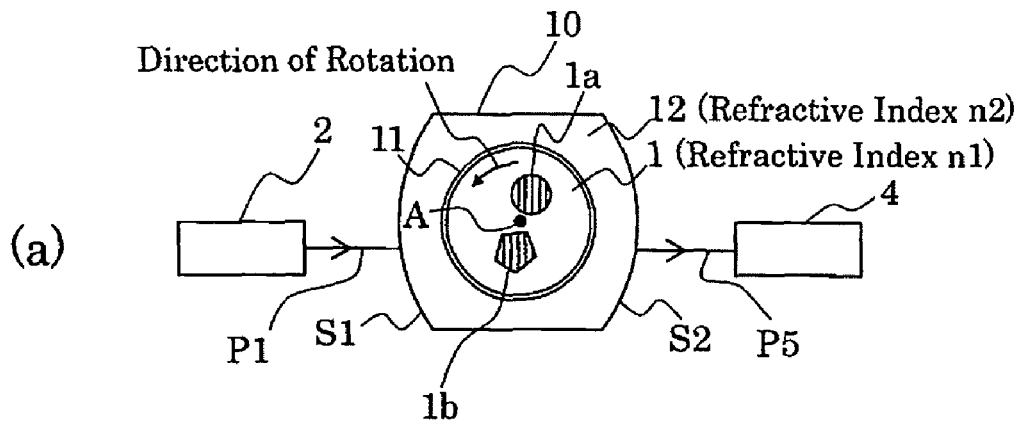
FIGS. 14(a) and 14(b) are plan views of the container 10 and the terahertz wave measurement device when the DUT 1 is rotated about the straight line A extending vertically (in the Z direction) as the rotational axis.
Figure 14:
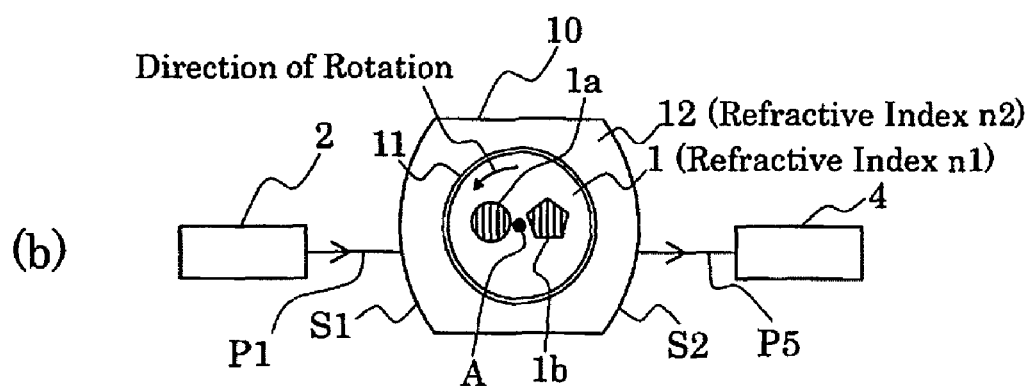
Figure 15:
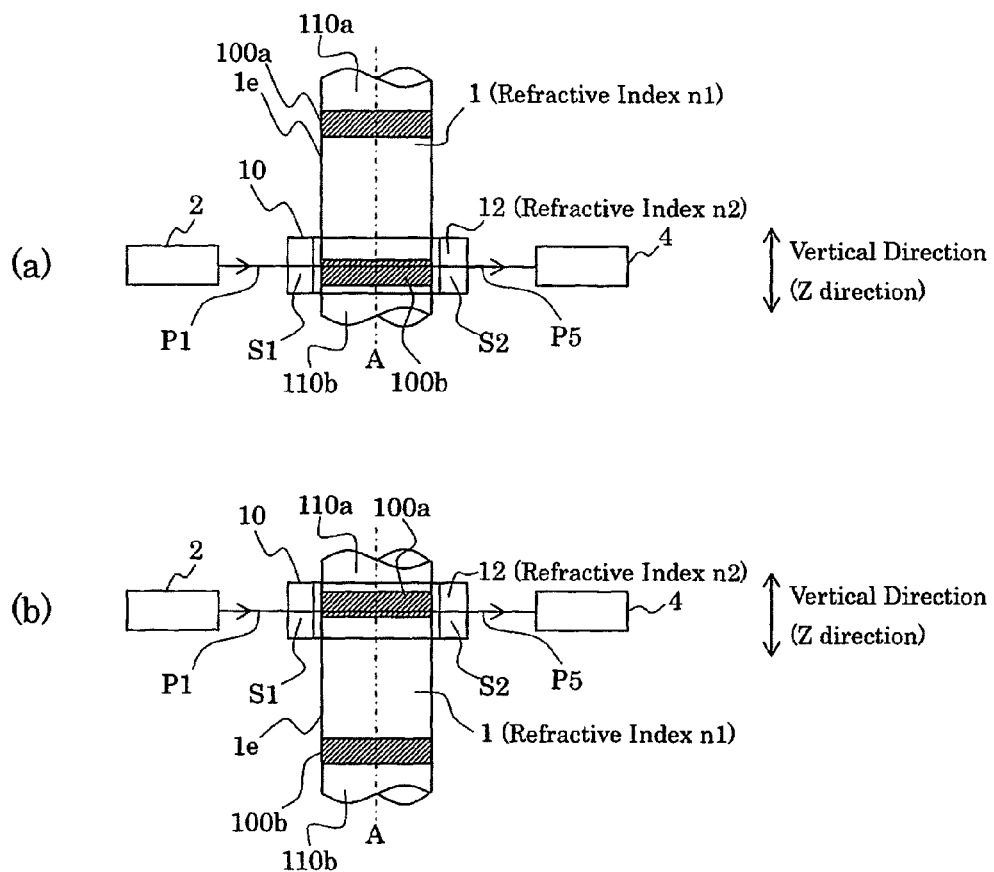
FIGS. 15(a) is a front view of the container 10, the fixtures 100a and 100b, the rotary actuators 110a and 110b, and the terahertz wave measurement device in the case in which the optical paths P1 and P5 of the terahertz wave are moved slightly below the end surface 1d of the DUT 1.
FIG. 15(b) is a front view of the container 10, the fixtures 100a and 100b, the rotary actuators 110a and 110b, and the terahertz wave measurement device in the case in which the optical paths P1 and P5 of the terahertz wave are moved slightly above the end surface 1c of the DUT 1.

The container 10 stores at least a part of the DUT 1 to be measured by the terahertz wave measurement device. It should be noted that the container 10 may store the DUT 1 partially (refer to FIGS. 10(*a*) and 10(*b*)) or entirely (refer to FIG. 19).

The container 10 includes a gap portion 11 and an enclosure portion 12. The gap portion 11 is a circular gap with a radius of r0 viewed from above (refer to FIG. 1). At least a part of the DUT 1 is disposed inside the gap portion 11 (refer to FIG. 2).

The enclosure portion 12 includes a first curved surface portion S1 and a second curved surface portion S2. The first curved surface portion S1 is a cylindrical surface with a radius of r1 (a part of a side surface of a cylinder the bottom surface of which is a circle with the radius of r1). The second curved surface portion S2 is a cylindrical surface with a radius of r2 (a part of a side surface of a cylinder the bottom surface of which is a circle with the radius of r2). It should be noted that the gap portion 11 is represented as a circle with the radius of r0, the first curved surface portion S1 is represented as an arc with the radius of r1 (>r0), and the second curved surface portion S2 is represented as an arc with the radius of r2 (=r1) in the plan view (FIG. 1(*a*)). All the centers of the circle and the arcs are present on an optical axis OA of the container 10. The center of the arc representing the first curved surface portion S1 and the center of the arc representing the second curved surface portion S2 are point symmetrical, and the center of the symmetry is the center of the circle representing the gap portion 11 in the plan view (FIG. 1(*a*)). Moreover, the arc representing the first curved surface portion S1 and the arc representing the second curved surface portion S2 are line symmetrical.

Though there has been given a description that the first curved surface portion S1 and the second curved surface portion S2 are the cylindrical surfaces, both or either of the first curved surface portion S1 and the second curved surface portion S2 may be non-cylindrical surface. This holds true for the other embodiments.

The gap portion 11 is arranged between the first curved surface portion S1 and the second curved surface portion S2. The enclosure portion 12 encloses the gap portion 11. On this occasion, a refractive index of the DUT 1 is denoted by n1, and a refractive index of the enclosure portion 12 is denoted by n2. Then, a relationship n1<n2 holds. Moreover, both the first curved surface portion S1 and the second curved surface portion S2 are convex surfaces. Moreover, n1 and n2 may not be equal to the refractive index (such as 1) of ambient air of the container 10.

It should be noted that the material of the enclosure portion 12 may be a resin material such as Teflon (registered trademark), polyethylene, and the like. These resin materials cannot usually be used for measurement of a light ray in the visible light area or the infrared light area. However, these resin materials present a little absorption and scatter of the light ray of the terahertz wave, and can thus be used for measurement by means of the terahertz wave.

Figure 3:
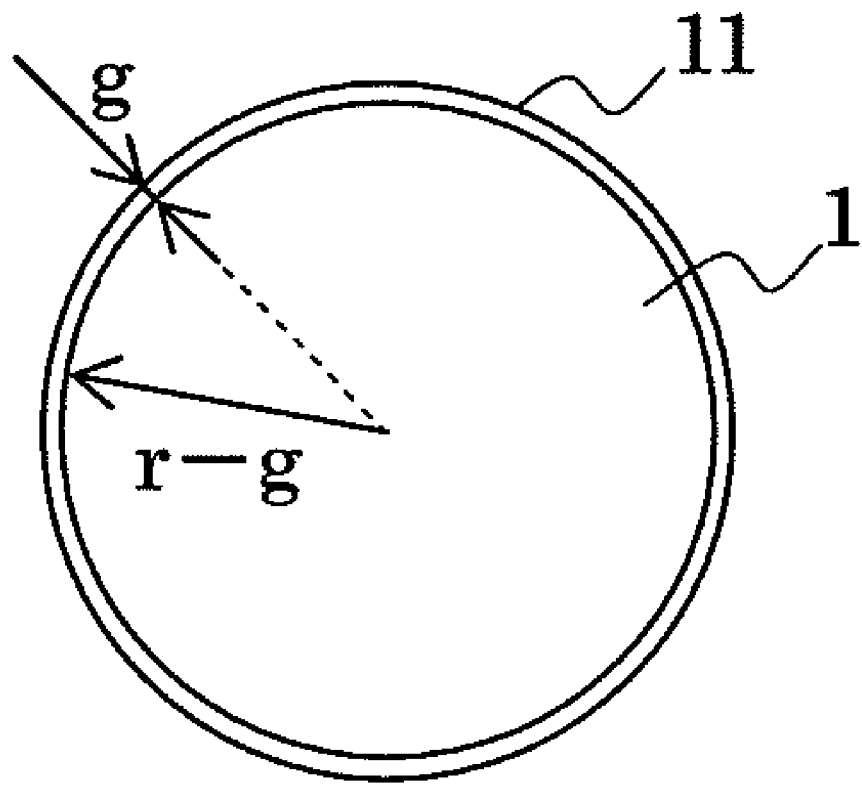
FIG. 3 is an enlarged plan view of the DUT 1 and the gap portion 11 when at least a part of the DUT 1 is stored in the container 10.

FIG. 3 is an enlarged plan view of the DUT 1 and the gap portion 11 when at least a part of the DUT 1 is stored in the container 10. The distance between a contour of a plane shape (shape viewed from above and a cross section on the plane) of the DUT 1 and a contour of the plane shape of the gap portion 11 (shape viewed from above and a cross section on the plane) is g. Then, the plane shape of the DUT 1 is a circle with a radius of r−g. Thus, the DUT 1 is a cylinder having a bottom surface of a circle with a radius of r−g.

It is preferable that a relationship $g \leq \lambda/4$ holds. It should be noted that $\lambda$ is the wavelength of the terahertz wave output from the terahertz wave output device 2 of the terahertz wave measurement device toward the DUT 1. When the relationship $g \leq \lambda/4$ holds, it is possible to restrain an air layer in the gap between the contour of the DUT 1 and the contour of the plane shape of the gap portion 11 from reflecting the terahertz wave. The reflection of the terahertz wave leads to a loss of the terahertz wave, and providing the relationship $g \leq \lambda/4$ leads to the restraint of the loss of the terahertz wave.

It should be noted that, referring to FIG. 2, the optical axis OA of the first curved surface portion S1 is configured so that it is parallel with the traveling direction (optical path P1) of the terahertz wave output from the terahertz wave output device 2 of the terahertz wave measurement device toward the DUT 1. The container 10 is provided as described above so as to measure the DUT 1 by the terahertz wave measurement device.

Figure 1:
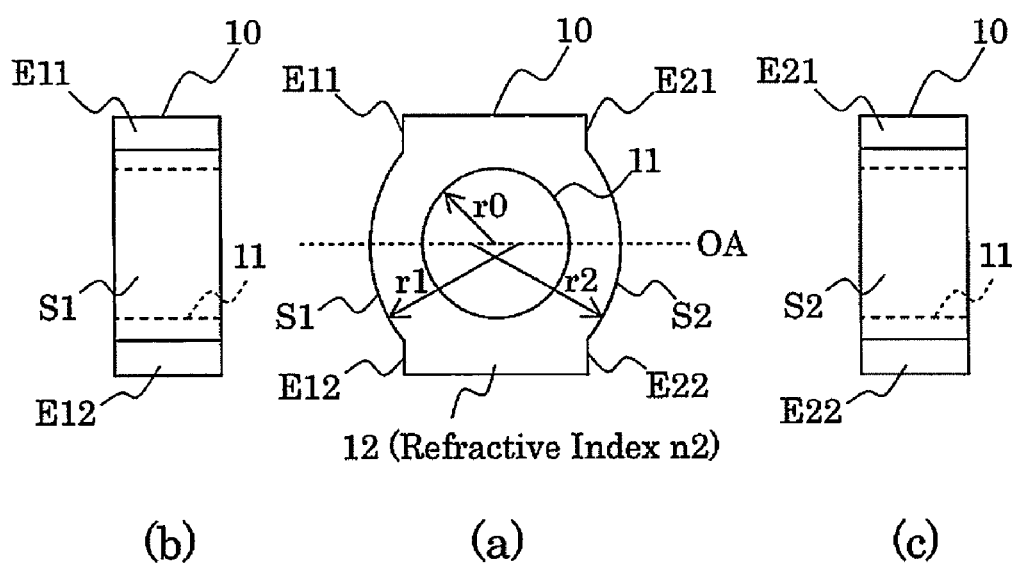
Figure 2:
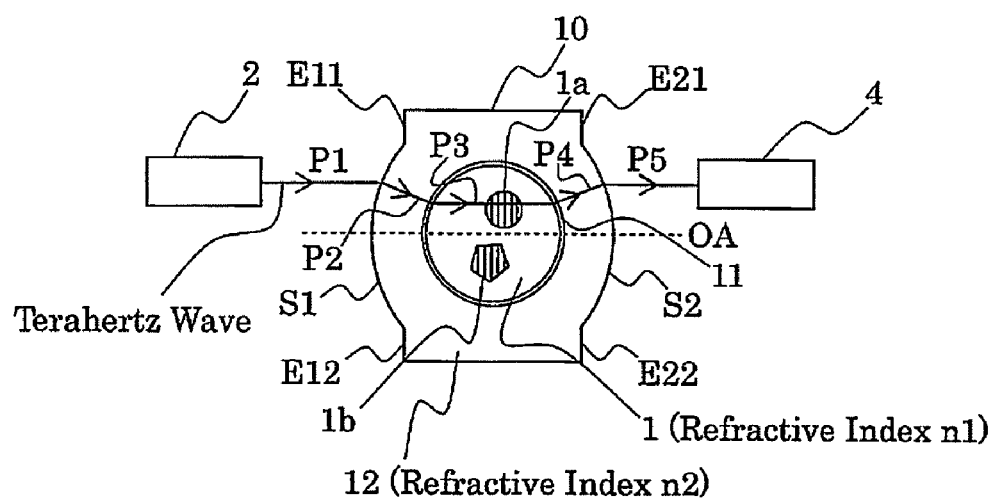
FIG. 2 is a plan view of a state in which at least a part of a device under test (DUT) 1 is stored in the container 10 according to the first embodiment of the present invention, and a terahertz wave is irradiated on the container 10.

Moreover, the enclosure portion 12 includes end portion flat surfaces E11 and E12 (on the side of the first curved surface portion S1) and end portion flat surfaces E21 and E22 (on the side of the second curved surface portion S2) on end portions (top and bottom in FIG. 1(*a*)). The end portion flat surfaces E11 and E12 and the end portion flat surfaces E21 and E22 are parallel with each other, and are orthogonal to the optical axis OA. Thus, even when the terahertz wave traveling on an optical path P1 parallel with the optical axis OA is made incident to the end portion flat surface E11 (or E12), the terahertz wave simply travels straight in the enclosure portion 12 (is not made incident to the DUT 1), and is emitted from the end portion flat surface E21 (or E22).

A description will now be given of an operation of the first embodiment.

Referring to FIG. 2, the terahertz wave output device 2 of the terahertz wave measurement device outputs the terahertz wave. The terahertz wave output from the terahertz wave output device 2 (optical path P1) is irradiated on the first curved surface portion S1. Then, the terahertz wave is refracted, and travels on an optical path P2 in the enclosure portion 12. On this occasion, the thickness of the air layer between the contour of the DUT 1 and the contour of the plane shape of the gap portion 11 is thin, and is thus neglected. The terahertz wave which has traveled on the optical path P2 is made incident to the DUT 1, is refracted, and travels on an optical path P3 inside the DUT 1. It should be noted that the optical path P3 is approximately parallel with the optical path P1 and the optical axis OA.

Figure 4:
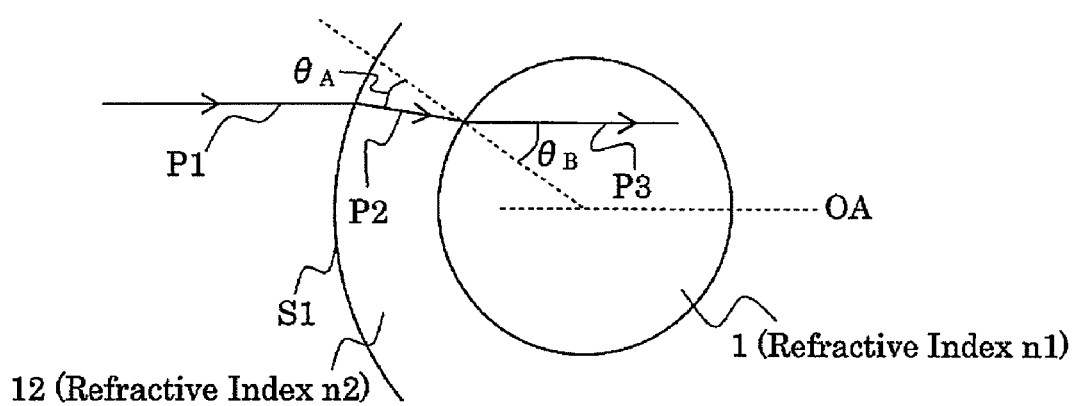
FIG. 4 is a plan view of the container 10 showing an enlarged neighborhood of the optical paths P1, P2, and P3 according to the first embodiment of the present invention.

FIG. 4 is a plan view of the container 10 showing an enlarged neighborhood of the optical paths P1, P2, and P3 according to the first embodiment of the present invention. It should be noted that the gap between the contour of the DUT 1 and the contour of the plane shape of the gap portion 11 is neglected, and the gap portion 11 is not illustrated.

Referring to FIG. 4, when the terahertz wave which has traveled on the optical path P1 is made incident to the first curved surface portion S1, the enclosure portion 12 serves as a convex lens, and the terahertz wave is refracted toward the optical axis OA. In FIG. 4, the terahertz wave travels downward (optical path P2). The terahertz wave which has traveled on the optical path P2 is made incident to the DUT 1, is refracted, and travels on the optical path P3.

On this occasion, the incident angle and the emission angle of the terahertz wave to and from the DUT 1 are respectively denoted by $\theta_A$ and $\theta_B$. According to Snell's law, a relationship $(\sin \theta_A)/(\sin \theta_B)=n1/n2$ holds. Moreover, since the relationship n1<n2 holds, a relationship n1/n2<1 holds. Therefore, a relationship $(\sin \theta_A)/(\sin \theta_B)<1$ holds. As a result, a relationship $\theta_A<\theta_B$ holds. Accordingly, the optical path P3 departs from the optical axis OA more than a straight extension of the optical path P2. On this occasion, the optical path P3 can be approximately parallel with the optical axis OA by properly setting n2 and the like.

Referring again to FIG. 2, the terahertz wave which has traveled on the optical path P3 inside the DUT 1 is made incident to the enclosure portion 12, is refracted, and travels on an optical path P4 in the enclosure portion 12. The terahertz wave which has traveled on the optical path P4 is made incident to the second curved surface portion S2, is refracted, travels on an optical path P5, and is made incident to the terahertz wave detector 4.

In FIG. 1(a), since the arc representing the first curved surface portion S1 and the arc representing the second curved surface portion S2 are line symmetrical, the optical path P2 and the optical path P4 are approximately line symmetrical, and the optical path P1 and the optical path P5 are approximately line symmetrical. Thus, the optical path P5 is approximately located on an extension of the optical path P1.

The terahertz wave detector 4 detects the incident terahertz wave. As a result, the DUT 1 is measured. For example, the DUT 1 includes contents 1a and 1b. Referring to FIG. 2, the terahertz wave transmits through the content 1a, and thus, the position and the like of the content 1a are revealed in a result of the detection by the terahertz wave.

According to the first embodiment, when the terahertz wave is fed to the DUT 1 for the measurement, though the terahertz wave is refracted by the DUT 1, the optical path P5 can be located by the container 10 approximately on the extension of the optical path P1. As a result, the terahertz wave made incident to the terahertz wave detector 4 is in a state approximately the same as that when the container 10 is not present, and the refraction by the DUT 1 does not occur. Thus, it is possible to restrain an adverse effect caused by the refraction of the terahertz wave by the DUT 1.

Second Embodiment

Shapes (concaved surfaces) of the first curved surface portion S1 and the second curved surface portion S2 of the container 10 according to a second embodiment are different from those (convex surfaces) of the first curved surface portion S1 and the second curved surface portion S2 of the container 10 according to the first embodiment.

Figure 5:
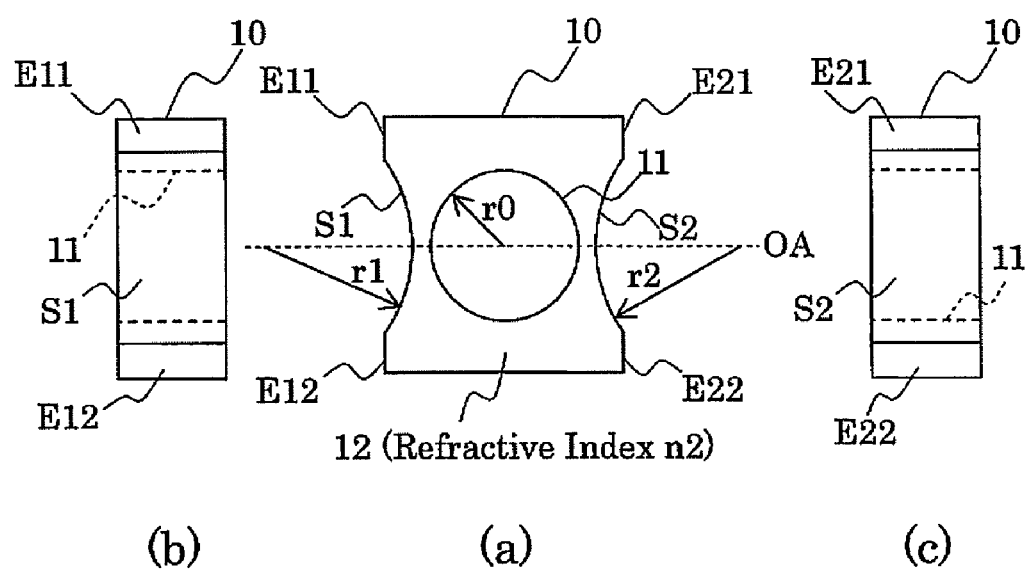
Figure 6:
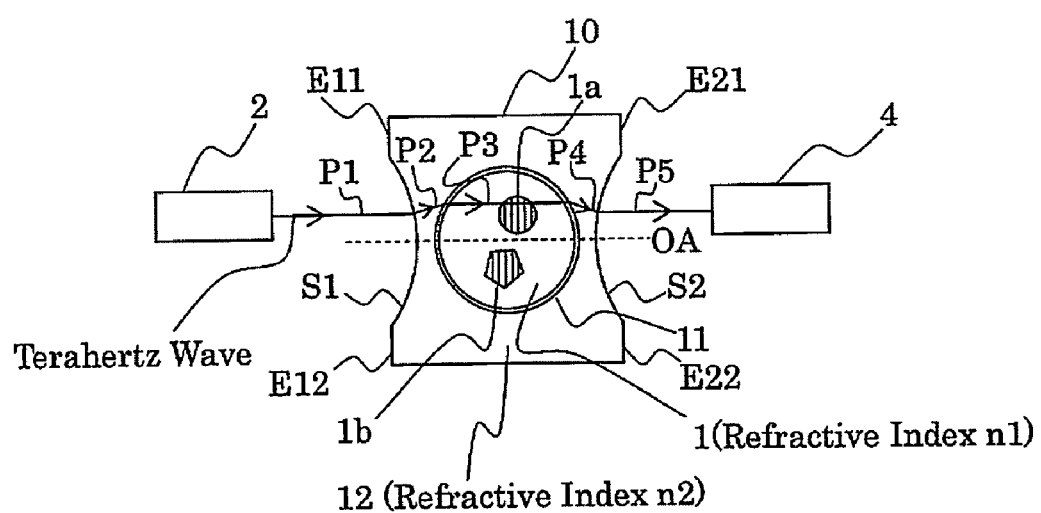
FIG. 6 is a plan view of a state in which at least a part of the DUT 1 is stored in the container 10 according to the second embodiment of the present invention, and the terahertz wave is irradiated on the container 10.

FIGS. 5(a) to 5(c) are views of the container 10 according to the second embodiment of the present invention, in which FIG. 5(a) is a plan view, FIG. 5(b) is a left side view, and FIG. 5(c) is a right side view. FIG. 6 is a plan view of a state in which at least a part of the DUT 1 is stored in the container 10 according to the second embodiment of the present invention, and the terahertz wave is irradiated on the container 10. In the following section, the same components are denoted by the same numerals as of the first embodiment, and will be explained in no more details.

The terahertz wave measurement device is the same as that of the first embodiment, and hence a description thereof is omitted.

The container 10 stores at least a part of the DUT 1 to be measured by the terahertz wave measurement device. It should be noted that the container 10 may store the DUT 1 partially (refer to FIGS. 10(a) and 10(b)) or entirely (refer to FIG. 19).

The container 10 includes the gap portion 11 and the enclosure portion 12. The gap portion 11 is the same as that of the first embodiment, and hence a description thereof is omitted.

The enclosure portion 12 includes the first curved surface portion S1 and the second curved surface portion S2. The enclosure portion 12 is the same as that of the first embodiment. However, both the first curved surface portion S1 and the second curved surface portion S2 according to the second embodiment are concave surfaces. It should be noted that the refraction index of the DUT 1 is n1, the refraction index of the enclosure portion 12 is n2, and a relationship n1>n2 holds.

A description will now be given of an operation of the second embodiment.

Referring to FIG. 6, the terahertz wave output device 2 of the terahertz wave measurement device outputs the terahertz wave. The terahertz wave output from the terahertz wave output device 2 (optical path P1) is irradiated on the first curved surface portion S1. Then, the terahertz wave is refracted, and travels on the optical path P2 in the enclosure portion 12. On this occasion, the thickness of the air layer between the contour of the DUT 1 and the contour of the plane shape of the gap portion 11 is thin, and is thus neglected. The terahertz wave which has traveled on the optical path P2 is made incident to the DUT 1, is refracted, and travels on the optical path P3 inside the DUT 1. It should be noted that the optical path P3 is approximately parallel with the optical path P1 and the optical axis OA.

Figure 7:
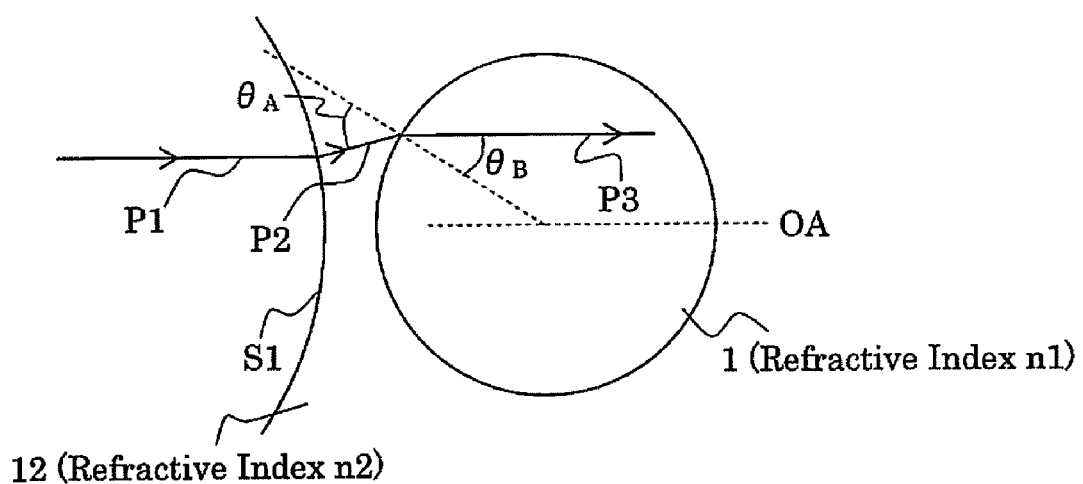
FIG. 7 is a plan view of the container 10 showing an enlarged neighborhood of the optical paths P1, P2, and P3 according to the second embodiment of the present invention.

FIG. 7 is a plan view of the container 10 showing an enlarged neighborhood of the optical paths P1, P2, and P3 according to the second embodiment of the present invention. It should be noted that the gap between the contour of the DUT 1 and the contour of the plane shape of the gap portion 11 is neglected, and the gap portion 11 is not illustrated.

Referring to FIG. 7, when the terahertz wave which has traveled on the optical path P1 is made incident to the first curved surface portion S1, the enclosure portion 12 serves as a concave lens, and the terahertz wave is refracted so as to depart from the optical axis OA. In FIG. 7, the terahertz wave travels upward (optical path P2). The terahertz wave which has traveled on the optical path P2 is made incident to the DUT 1, is refracted, and travels on the optical path P3.

On this occasion, the incident angle and the emission angle of the terahertz wave to and from the DUT 1 are respectively denoted by $\theta_A$ and $\theta_B$. According to Snell's law, the relationship $(\sin \theta_A)/(\sin \theta_B)=n1/n2$ holds. Moreover, since the relationship n1>n2 holds, a relationship n1/n2>1 holds. Therefore, a relationship $(\sin \theta_A)/(\sin \theta_B)>1$ holds. As a result, a relationship $\theta_A>\theta_B$ holds. Accordingly, the optical path P3 approaches the optical axis OA more than a straight extension of the optical path P2. On this occasion, the optical path P3 can be approximately parallel with the optical axis OA by properly setting n2 and the like.

Referring again to FIG. 6, the terahertz wave which has traveled on the optical path P3 inside the DUT 1 is made incident to the enclosure portion 12, is refracted, and travels on an optical path P4 in the enclosure portion 12. The terahertz wave which has traveled on the optical path P4 is made incident to the second curved surface portion S2, is refracted, travels on the optical path P5, and is made incident to the terahertz wave detector 4.

In FIG. 6, since the arc representing the first curved surface portion S1 and the arc representing the second curved surface portion S2 are line symmetrical, the optical path P2 and the optical path P4 are approximately line symmetrical, and the optical path P1 and the optical path P5 are approximately line symmetrical. Thus, the optical path P5 is approximately located on an extension of the optical path P1.

The terahertz wave detector 4 detects the incident terahertz wave. As a result, the DUT 1 is measured. For example, the DUT 1 includes contents 1a and 1b. Referring to FIG. 2, the terahertz wave transmits through the content 1a, and thus, the position and the like of the content 1a are revealed in a result of the detection by the terahertz wave.

According to the second embodiment, there are obtained the same effects as in the first embodiment.

Third Embodiment

The container 10 according to a third embodiment of the present invention approximately corresponds to a case in which the enclosure portions 12a and 12b of the container 10 according to the first and second embodiments are different from each other in shape.

Figure 8:
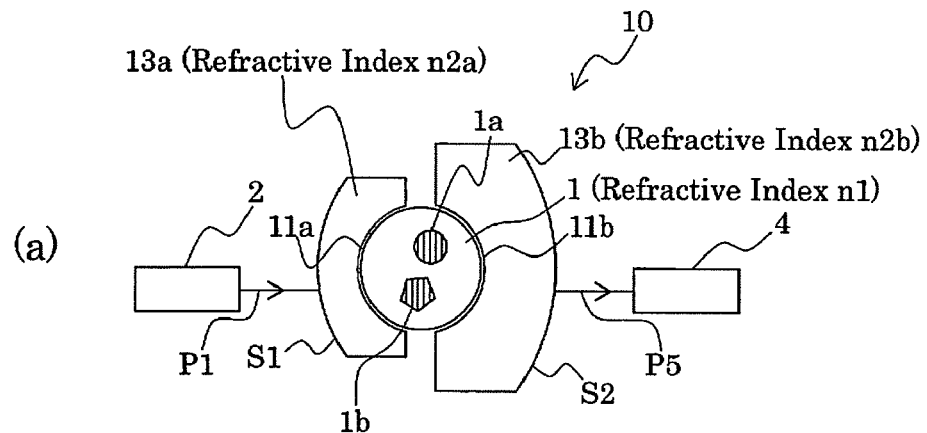
FIGS. 8(a) and 8(b) are plan views of the container 10 according to the third embodiment of the present invention.
Figure 8:
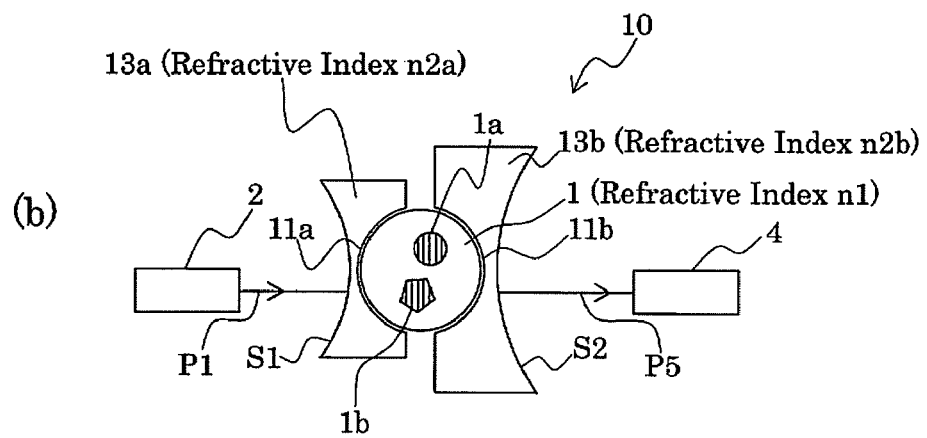

FIGS. 8(a) and 8(b) are plan views of the container 10 according to the third embodiment of the present invention. It should be noted that FIG. 8(a) is a plan view of the container 10 when relationships n2a>n1 and n2b>n1 hold. FIG. 8(b) is a plan view of the container 10 when relationships n2a<n1 and n2b<n1 hold.

The terahertz wave measurement device is the same as that of the first embodiment, and hence a description thereof is omitted. It should be noted that the electromagnetic wave to be measured, which is to be output and detected by the terahertz wave measurement device (electromagnetic wave measurement device), is not limited to the terahertz wave, and may be an electromagnetic wave the frequency of which is equal to or more than 0.01 [THz] and equal to or less than 100 [THz] as in the first embodiment.

The container 10 stores at least a part of the DUT 1 to be measured by the terahertz wave measurement device. It should be noted that the container 10 may store the DUT 1 partially (refer to FIGS. 10(a) and 10(b)) or entirely (refer to FIG. 19).

The container 10 includes a first cover portion 13a and a second cover portion 13b. A material of the first cover portion 13a and the second cover portion 13b may be the same as the material of the enclosure portion 12.

The refractive index of the first cover portion 13a is n2a. The first cover portion 13a includes the first curved surface portion S1 (same as the first and second embodiments), and a first concave surface portion 11a. The first curved surface portion S1 receives the terahertz wave output from the terahertz wave output device 2 of the terahertz wave measurement device toward the DUT 1. The first concave surface portion 11a is closer to the DUT 1 than the first curved surface portion S1, and transmits the terahertz wave.

On this occasion, when n2a is larger than n1 (refraction index of the DUT 1), referring to FIG. 8(a), the first curved surface portion S1 is a convex surface. The specific shape of the first curved surface portion S1 is the same as that of the first embodiment.

When n2a is less than n1, referring to FIG. 8(b), the first curved surface portion S1 is a concave surface. The specific shape of the first curved surface portion S1 is the same as that of the second embodiment.

The refractive index of the second cover portion 13b is n2b. The second cover portion 13b includes the second curved surface portion S2 (same as the first and second embodiments), and a second concave surface portion 11b. The second concave surface portion 11b receives the terahertz wave which has transmitted through the DUT 1. The second curved surface portion S2 is farther than the second concave surface portion 11b from the DUT 1, and transmits the terahertz wave.

On this occasion, when n2b is larger than n1, referring to FIG. 8(a), the second curved surface portion S2 is a convex surface. The specific shape of the second curved surface portion S2 is the same as that of the first embodiment.

When n2b is less than n1, referring to FIG. 8(b), the second curved surface portion S2 is a concave surface. The specific shape of the second curved surface portion S2 is the same as that of the second embodiment.

It should be noted that n2a and n2b are different from each other. Moreover, the curvature radius of the plane shape of the first curved surface portion S1 and the curvature radius of the plane shape of the second curved surface portion S2 are different from each other. In FIGS. 8(a) and 8(b), the curvature radius of the plane shape of the second curved surface portion S2 is larger than the curvature radius of the plane shape of the first curved surface portion S1.

Moreover, the contours of the plane shapes of the first concave surface portion 11a and the second concave surface portion 11b are arcs. A distance between the contours of the plane shapes of the first concave surface portion 11a and the second concave surface portion 11b, and the contour of the plane shape of the DUT 1 is g1. It should be noted that a relationship $g1 \leq \lambda/4$ preferably holds as in the first embodiment (refer to FIG. 3).

It should be noted that the optical axis OA (which is the same as that in FIG. 2, and is thus omitted) of the first curved surface portion S1 is also made parallel with the traveling direction (optical path P1) of the terahertz wave output from the terahertz wave output device 2 of the terahertz wave measurement device toward the DUT 1 as in the first embodiment (refer to FIG. 2).

A description will now be given of an operation of the third embodiment.

When the container 10 shown in FIG. 8(a) is used, the terahertz wave travels on the optical paths similar to those of the first embodiment. It should be noted that, by properly setting the curvature radii of the plane shapes of the first curved surface portion S1 and the second curved surface portion S2, n2a, and n2b, the optical path P5 is situated approximately on the extension of the optical path P1.

When the container 10 shown in FIG. 8(b) is used, the terahertz wave travels on the optical paths similar to those of the second embodiment. It should be noted that, by properly setting the curvature radii of the plane shapes of the first curved surface portion S1 and the second curved surface portion S2, n2a, and n2b, the optical path P5 is situated approximately on the extension of the optical path P1.

According to the third embodiment, there are obtained the same effects as in the first embodiment.

As the third embodiment, the description has been given of the case in which the relationships n1<n2a and n1<n2b hold (refer to FIG. 8(a)), and the case in which the relationships n1>n2a and n1>n2b hold (refer to FIG. 8(b)). However, a case in which relationships n1<n2a and n1>n2b hold, and a case in which relationships n1>n2a and n1<n2b hold are conceivable.

Figure 9:
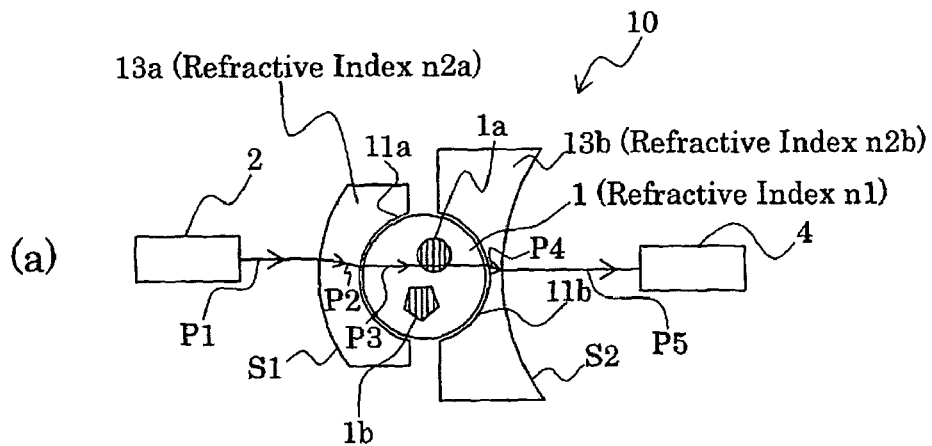
FIGS. 9(a) and 9(b) show variations of the third embodiment.
Figure 9:
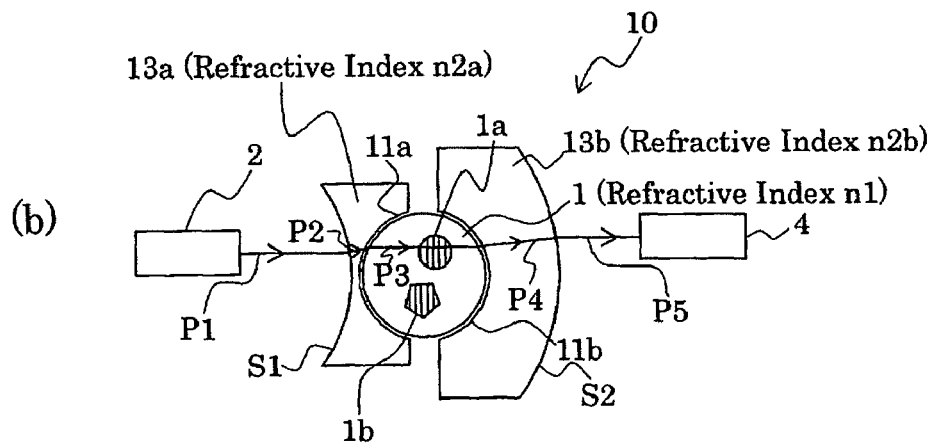

FIGS. 9(a) and 9(b) show variations of the third embodiment. It should be noted that FIG. 9(a) is a plan view of the container 10 when the relationships n1<n2a and n1>n2b hold. FIG. 9(b) is a plan view of the container 10 when the relationships n1>n2a and n1<n2b hold.

In FIG. 9(a), the first curved surface portion S1 is a convex surface and the second curved surface portion S2 is a concave surface. The optical paths P1, P2, and P3 are the same as those of the first embodiment (refer to FIG. 2), and the optical paths P4 and P5 are the same as those of the second embodiment (refer to FIG. 6). Though the optical path P5 is not situated on the extension of the optical path P1, the optical path P5 and the optical path P1 can be approximately parallel with each other.

In FIG. 9(b), the first curved surface portion S1 is a concave surface and the second curved surface portion S2 is a convex surface. The optical paths P1, P2, and P3 are the same as those of the second embodiment (refer to FIG. 6), and the optical paths P4 and P5 are the same as those of the first embodiment (refer to FIG. 2). Though the optical path P5 is not situated on the extension of the optical path P1, the optical path P5 and the optical path P1 can be approximately parallel with each other.

Fourth Embodiment

According to a fourth embodiment, the DUT 1 is fixed to fixtures 100a and 100b, and the DUT 1 is scanned while the DUT 1 is rotated along with the fixtures 100a and 100b.

FIGS. 10(a) and 10(b) are front views of the container 10, the fixtures 100a and 100b, rotary actuators 110a and 110b, and the terahertz wave measurement device according to the fourth embodiment. Configurations of the container 10 and the terahertz wave measurement device according to the fourth embodiment are approximately the same as those according to the first to third embodiments. However, the DUT 1 is cylindrical, and a part of the DUT 1 is stored in the gap portion 11 of the container 10.

It should be noted that FIGS. 10(a) and 10(b) show a configuration in which the container 10 according to the first embodiment is used along with the fixtures 100a and 100b. However, the containers 10 according to the second and third embodiments may be used along with the fixtures 100a and 100b. It should be noted that the same applied to FIGS. 11(a) to 19.

When refractive indices of the fixtures 100a and 100b are n0 and the refractive index of the DUT 1 is n1, a relationship n0=n1 holds. It should be noted that as long as a relationship n1−0.1≦n0≦n1+0.1 holds, effects of the fixtures 100a and 100b can be provided (refer to FIG. 16).

The cylindrical DUT 1 includes end surfaces 1c and 1d (refer to FIGS. 11(a) to 12(d)), and a side surface 1e. The side surface 1e is a curved surface between the end surfaces 1c and 1d. The side surface 1e is not covered by the fixtures 100a and 100b.

FIGS. 11(a) to 11(d) are views of the fixtures 100a and the DUT 1, in which FIG. 11(a) is a front view of the fixture 100a, FIG. 11(b) is a bottom view of the fixture 100a, FIG. 11(c) is a plan view of the DUT 1, and FIG. 11(d) is a front view of the DUT 1. FIGS. 12(a) to 12(d) are views of the DUT 1 and fixtures 100b, in which FIG. 12(a) is a front view of the DUT 1, FIG. 12(b) is a bottom view of the DUT 1, FIG. 11(c) is a plan view of the fixture 100b, and FIG. 12(d) is a front view of the fixture 100b.

Referring to FIGS. 11(a) to 11(d), the fixture 100a is cylindrical, and the bottom surface (fixing surface) 102a thereof is circular. The upper end surface 1c of the DUT 1 is also circular. The bottom surface (fixing surface) 102a and the end surface is have the same shape.

Referring to FIGS. 12(a) to 12(d), the fixture 100b is cylindrical, and the top surface (fixing surface) 102b thereof is circular. The lower end surface 1d of the DUT 1 is also circular. The top surface (fixing surface) 102b and the end surface 1d have the same shape.

It should be noted that the end surfaces 1c and 1d are parallel with each other.

On this occasion, referring to FIGS. 10(a) to 12(d), the upper end surface 1c of the DUT 1 is fixed to the bottom surface (fixing surface) 102a of the fixture 100a. The bottom end surface 1d of the DUT 1 is fixed to the top surface (fixing surface) 102b of the fixture 100b.

The two fixtures 100a and 100b are respectively pressed against the two end surfaces 1c and 1d. In other words, (the bottom surface 102a of) the fixture 100a is pressed against the end surface 1c and (the top surface 102b of) the fixture 100b is pressed against the end surface 1d.

As a result of this pressing, the DUT 1 will not vertically move with respect to the fixtures 100a and 100b. Moreover, due to friction forces between the end surfaces 1c and 1d and the bottom surface 102a and top surface 102b, the DUT 1 will not move in directions orthogonal to the vertical direction with respect to the fixtures 100a and 100b. In other words, the end surfaces 1c and 1d are fixed to the bottom surface 102a and top surface 102b.

It should be noted that the end surface may be fixed to the bottom and/or top surface by adhering one or both of the end surface 1c and the end surface 1d to one or both of the bottom surface 102a and the top surface 102b (using a widely known adhesive, for example).

The rotary actuator 110a is connected to the DUT 1 via the fixture 100a. The rotary actuator 110a is rotated about a straight line A orthogonal to the bottom surface 102a as an axis.

The rotary actuator 110b is connected to the DUT 1 via the fixture 100b. The rotary actuator 110b is rotated about the straight line A orthogonal to the top surface 102b as an axis.

It is assumed that the bottom surface 102a and the top surface 102b are parallel with each other.

A description will now be given of an operation of the fourth embodiment.

Referring to FIG. 10(a), the terahertz wave output device 2 of the terahertz wave measurement device outputs the terahertz wave (referred to as "output step" hereinafter). The output terahertz wave transmits through the enclosure portion 12 and the DUT 1 while traveling on the optical paths P1 to P5 as described in the first embodiment, and is detected by the terahertz wave detector 4 of the terahertz wave measurement device (referred to as "detection step" hereinafter). As a result, the DUT 1 is measured by the terahertz wave measurement device.

As shown in FIG. 10(a), while Z coordinates (it should be noted that a Z direction is the vertical direction) of the terahertz wave measurement device and the DUT 1 are fixed, the container 10 and the DUT 1 are moved in the horizontal direction (X direction) with respect to the optical paths P1 and P5 of the terahertz wave (refer to FIGS. 13(a) and 13(b)), and the DUT 1 is rotated about the straight line A (refer to FIGS. 10(a) and 10(b)) extending in the vertical direction (Z direction) as a rotational axis (the straight line A may not be an actual member) (refer to FIGS. 14(a) and 14(b)). In this way, the DUT 1 can be measured by means of the widely known computer tomography (CT) on a cross section on a plane orthogonal to the straight line A.

FIGS. 13(a) and 13(b) are plan views of the container 10 and the terahertz wave measurement device when the container 10 and the DUT 1 are moved in the X direction.

Referring to FIG. 13(a), during the output step and the detection step, the container 10 and the DUT 1 are moved horizontally (downward in FIGS. 13(a) and 13(b)) with respect to the optical paths P1 and P5 of the terahertz wave. As a result, as shown in FIG. 13(b), the optical paths P1 and P5 intersect with a certain portion of the DUT 1 (which is different from that in FIG. 13(a)).

During the output step and the detection step, a similar effect can be provided if the optical paths P1 and P5 of the terahertz wave are moved horizontally with respect to the container 10 and the DUT 1 (upward in FIGS. 13(a) and 13(b)). In order to move the optical paths P1 and P5 of the terahertz wave, the terahertz wave output device 2 and the terahertz wave detector 4 may be moved.

FIGS. 14(a) and 14(b) are plan views of the container 10 and the terahertz wave measurement device when the DUT 1 is rotated about the straight line A extending vertically (in the Z direction) as the rotational axis.

Referring to FIG. 14(a), the output step is carried out. The output terahertz wave transmits through the enclosure portion 12 and the DUT 1 while traveling on the optical paths P1 to P5 as described according to the first embodiment. Then, the detection step is carried out. As a result, a certain part of the DUT 1 is measured by the terahertz wave measurement device.

While the output step and the detection step are carried out, the DUT 1 is rotated about the straight line A extending vertically (in the Z direction) (refer to FIGS. 10(a) and 10(b)) as the rotational axis (straight line A may not be an actual member). For example, the DUT 1 is rotated counterclockwise. Then, the DUT 1 is arranged as shown in FIG. 14(b). The part of the DUT 1 which intersects with the optical path P2 is different between the case in FIG. 14(b) and the case in FIG. 14(a). Thus, the case in FIG. 14(b) and the case in FIG. 14(a) can respectively measure different parts of the DUT 1.

In order to rotate the DUT 1 about the straight line A as the rotational axis, the fixtures 100a and 100b may be rotated about the straight line A as the rotational axis. It should be noted that the straight line A is a straight line orthogonal to the bottom surface 102a and the top surface 102b (fixing surfaces). In order to rotate the fixtures 100a and 100b, the rotary actuators 110a and 110b may be rotated.

Referring to FIGS. 10(a) and 10(b), the travel direction of the electromagnetic wave to be measured (direction of the optical path P1) is orthogonal to the straight line A.

As described above, in the state shown in FIG. 10(a), while the container 10 and the DUT 1 (or the terahertz wave output device 2 and the terahertz wave detector 4) are moved in the X direction, the DUT 1 is rotated about the straight line A as the rotational axis. After this process, a cross section of the DUT 1 on the plane (plane containing the optical path P1 in FIG. 10(a)) orthogonal to the Z direction can be measured by means of the widely known CT.

Further, the container 10 and the optical paths P1 and P5 of the terahertz wave are moved upward with respect to the DUT 1. Then, the optical paths P1 and P5 intersect with an upper part of the DUT 1 as shown in FIG. 10(b).

In the state shown, while the container 10 and the DUT 1 (or the terahertz wave output device 2 and the terahertz wave detector 4) are moved in the X direction, the DUT 1 is rotated about the straight line A as the rotational axis. After this process, a cross section of the DUT 1 on a plane (plane containing the optical path P1 in FIG. 10(b)) orthogonal to the Z direction can be measured by means of the widely known CT.

It should be noted that, in order to move the optical paths P1 and P5 of the terahertz wave, the terahertz wave output device 2 and the terahertz wave detector 4 may be moved. Alternatively, the DUT 1 may vertically be moved with respect to the container 10 and the optical paths P1 and P5 of the terahertz wave.

While the optical paths P1 and P5 of the terahertz wave are vertically moved between the end surfaces 1c and 1d of the DUT 1 (the container 10 is also vertically moved along with the optical paths of the terahertz wave), cross sections of the DUT 1 on planes orthogonal to the Z directions are measured. As a result, the DUT 1 can be measured.

On this occasion, the optical paths P1 and P5 of the terahertz wave may be moved slightly below the end surface 1d of the DUT 1. Alternatively, the optical paths P1 and P5 of the terahertz wave may be moved slightly above the end surface 1c of the DUT 1.

FIG. 15(a) is a front view of the container 10, the fixtures 100a and 100b, the rotary actuators 110a and 110b, and the terahertz wave measurement device in the case in which the optical paths P1 and P5 of the terahertz wave are moved slightly below the end surface 1d of the DUT 1, and FIG. 15(b) is a front view of the container 10, the fixtures 100a and 100b, the rotary actuators 110a and 110b, and the terahertz wave measurement device in the case in which the optical paths P1 and P5 of the terahertz wave are moved slightly above the end surface 1c of the DUT 1.

It should be noted that FIGS. 15(a) and 15(b) are views looking transparently through the container 10 and showing the DUT 1, the fixtures 100a and 100b, and the rotary actuators 110a and 110b inside the container 10.

In the case shown in FIGS. 15(a) and 15(b), the terahertz wave output from the terahertz wave output device 2 transmits through the fixture 100a or 100b, and is detected by the terahertz wave detector 4.

Figure 16:
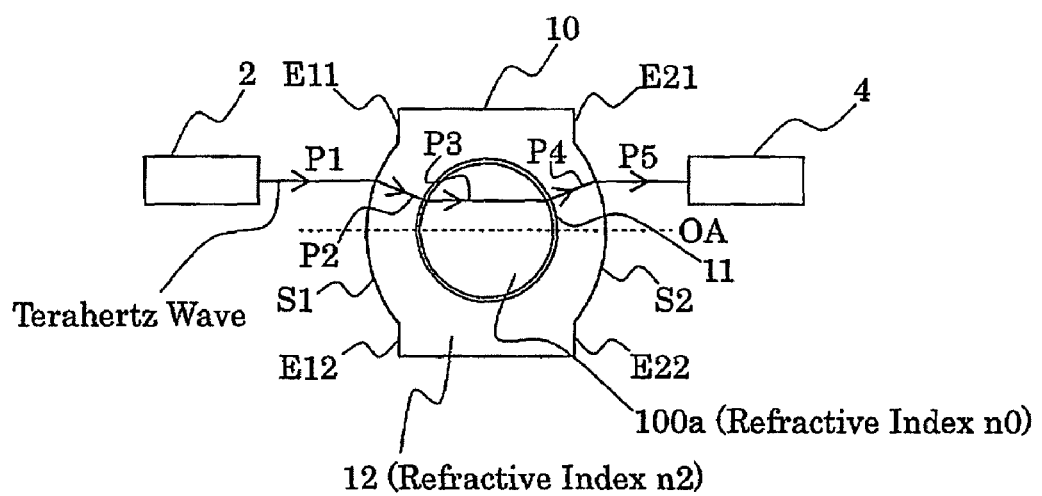
FIG. 16 is a plan cross sectional view of the container 10 and the fixture 100a in FIGS. 15(a) and 15(b)

FIG. 16 is a plan cross sectional view of the container 10 and the fixture 100a in FIGS. 15(a) and 15(b). It should be noted that FIG. 16 shows a cross section of the container 10 and the fixture 100a in FIG. 15(b) on a plane orthogonal to the Z direction (plane containing the optical path P1 in FIG. 15(b)). Moreover, the refractive index n0 of the fixture 100a is equal to the refractive index n1 of the DUT 1.

Since the refractive index n0 of the fixture 100a is equal to the refractive index n1 of the DUT 1, the optical paths P1 to P5 of the terahertz wave are the same as those shown in FIG. 2.

When the terahertz wave output from the terahertz wave output device 2 transmits through the fixture 100b (corresponding to FIG. 15(a)), the optical paths of the terahertz wave are similar to those in FIG. 16 (and FIG. 2). It is assumed that the refractive index n0 of the fixture 100b is equal to the refractive index n1 of the DUT 1.

As long as the relationship $n1-0.1 \leq n0 \leq n1+0.1$ holds, the optical paths of the terahertz wave transmitting through the fixture 100a and the optical paths of the terahertz wave transmitting through the fixture 100b are approximately the same as those in FIG. 16 (and FIG. 2).

Figure 17:
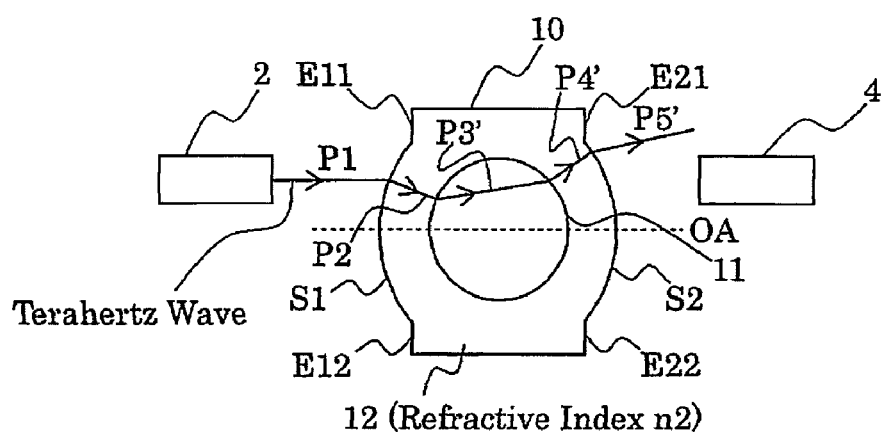
FIG. 17 is a plan cross sectional view of the container 10 in a comparative example assuming that the fixture 100a in FIG. 15(b) is not present.

FIG. 17 is a plan cross sectional view of the container 10 in a comparative example assuming that the fixture 100a in FIG. 15(b) is not present. It should be noted that FIG. 17 shows the cross section of the container 10 in FIG. 15(b) on the plane orthogonal to the Z direction (plane containing the optical path P1 in FIG. 15(b)). It should be noted that a relationship $1 < n1 < n2$ holds.

The optical paths P1 and P2 are the same as those in FIG. 2. However, since the relationship 1<n1 holds, an optical path P3' departs away from the optical axis OA more than the optical path P3. The terahertz wave which has traveled on the optical path P3' travels on optical paths P4' and P5', and departs away from the optical axis OA. As a result, the terahertz wave cannot be detected by the terahertz wave detector 4.

This means that, if the optical paths P1 and P5 of the terahertz wave are moved slightly above the end surface is of the DUT 1 (refer to FIG. 15(b)), and the fixture 100a is not present, the terahertz wave cannot be detected by the terahertz wave detector 4.

Similarly, if the optical paths P1 and P5 of the terahertz wave are moved slightly below the end surface 1d of the DUT 1 (refer to FIG. 15(a)), and the fixture 100b is not present, the terahertz wave cannot be detected by the terahertz wave detector 4.

Then, when a neighborhood of the end surface 1c or 1d of the DUT 1 is to be measured, if the optical paths P1 and P5 of the terahertz wave are displaced from the DUT 1 even slightly, the terahertz wave is no longer detected by the terahertz wave detector 4. It is not preferable for the measurement of the neighborhoods of the end surfaces 1c and 1d of the DUT 1.

However, according to the fourth embodiment, the fixtures 100a and 100b exist. As a result, even if the optical paths P1 and P5 of the terahertz wave are slightly displaced from the DUT 1, the optical paths of the terahertz wave are formed as shown in FIG. 16, which is the same as those in FIG. 2. Therefore, even if the optical paths P1 and P5 of the terahertz wave are slightly displaced from the DUT 1, the terahertz wave can be detected by the terahertz wave detector 4. It is preferable for the measurement of the neighborhoods of the end surfaces 1c and 1d of the DUT 1.

As described before, the side surface 1e of the DUT 1 is not covered by the fixtures 100a and 100b. This configuration provides the following advantageous effects.

Figure 18:
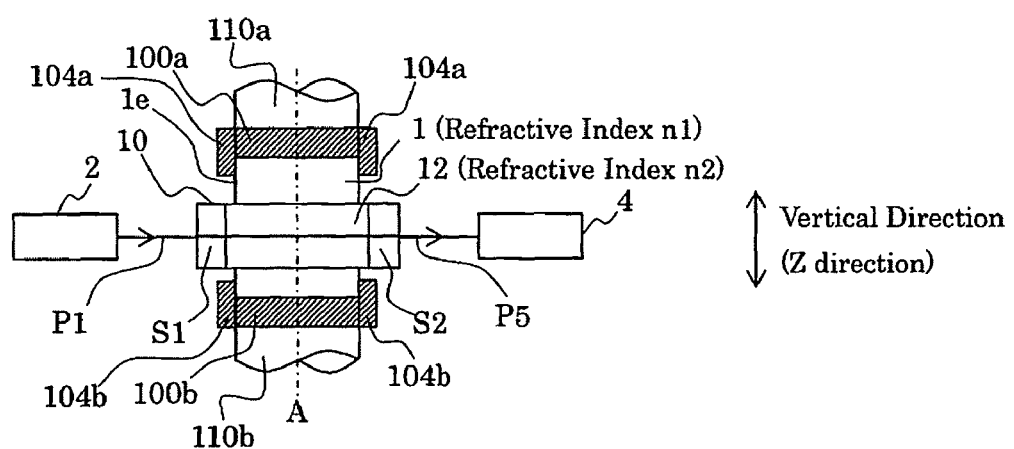
FIG. 18 is a front view of the container 10, the fixtures 100a and 100b, the rotary actuators 110a and 110b, and the terahertz wave measurement device in a comparative example assuming that the side surface 1e of the DUT 1 is covered by the fixtures 100a and 100b in FIGS. 10(a) and 10(b)

FIG. 18 is a front view of the container 10, the fixtures 100a and 100b, the rotary actuators 110a and 110b, and the terahertz wave measurement device in a comparative example assuming that the side surface 1e of the DUT 1 is covered by the fixtures 100a and 100b in FIGS. 10(a) and 10(b).

In this comparative example, if the neighborhoods of the end surfaces 1c and 1d of the DUT 1 are measured, side-surface covering portions 104a and 104b with the side surface 1e covered by the fixtures 100a and 100b (the DUT 1 is fixed to the fixtures 100a and 100b by the side-surface covering portions 104a and 104b clamping the side surface 1e of the DUT 1) collide with the container 10. Moreover, when the terahertz wave transmits through the side-surface covering portion 104a or 104b, the travel direction of the terahertz wave changes due to the presence of the side-surface covering portion 104a or 104b, and the terahertz wave may not be detected by the terahertz wave detector 4.

However, according to the fourth embodiment, the side surface 1e of the DUT 1 is not covered by the fixtures 100a and 100b, and the states in which the side-surface covering portions 104a and 104b collide with the container 10, and the terahertz wave detector 4 cannot detect the terahertz wave are thus avoided.

According to the fourth embodiment, the description is given of the example in which a part of the DUT 1 is stored in the gap portion 11 of the container 10 (refer to FIGS. 10(a) and 10(b)). However, the DUT 1 may entirely be stored in the gap portion 11 of the container 10.

Figure 19:
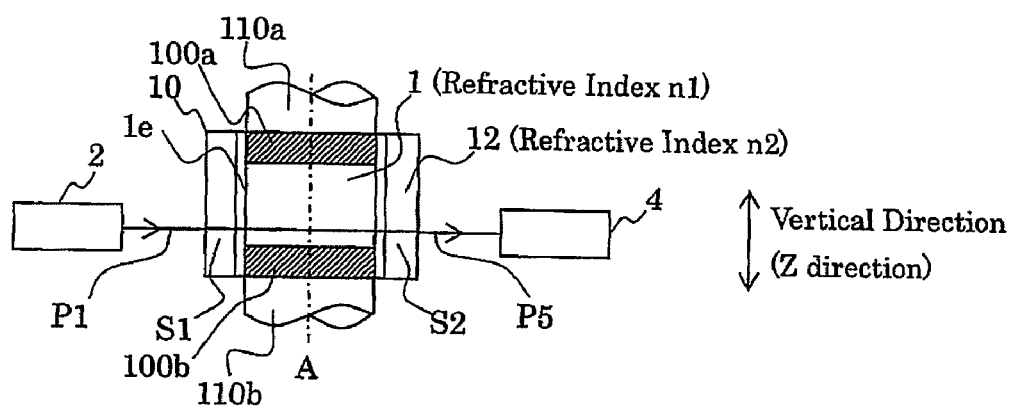
FIG. 19 is a front view of the container 10, the fixtures 100a and 100b, rotary actuators 110a and 110b, and the terahertz wave measurement device according to a variation of the fourth embodiment.
Figure 20:
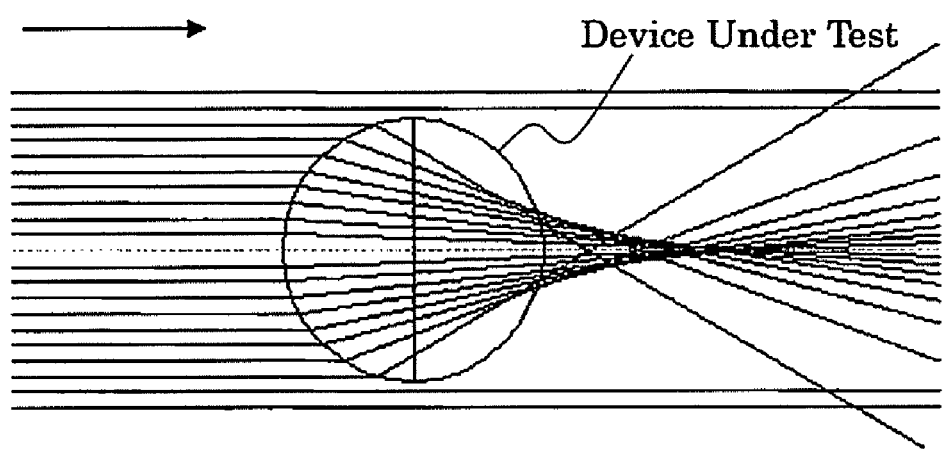
FIG. 20 shows estimated optical paths of the terahertz wave when the refractive index of a conventional device under test is 1.4, and the refractive index of the ambient air of the device under test is 1.

FIG. 19 is a front view of the container 10, the fixtures 100a and 100b, rotary actuators 110a and 110b, and the terahertz wave measurement device according to a variation of the fourth embodiment. It should be noted that FIG. 19 is a view looking transparently through the container 10 and showing the DUT 1 and the fixtures 100a and 100b inside the container 10.

The DUT 1 is cylindrical, and the entirety of the DUT 1 is stored in the gap portion 11 of the container 10.

In the variation of the fourth embodiment shown in FIG. 19, the container 10 and the DUT 1 are moved vertically with respect to the optical paths P1 and P5 of the terahertz wave. Alternatively, the optical paths P1 and P5 of the terahertz wave may vertically be moved with respect to the container 10 and the DUT 1.

According to the fourth embodiment, the description is given of the example in which the fixtures 100a and 100b are used along with the container 10. However, the fixtures 100a and 100b may be used without the container 10.

Moreover, according to the fourth embodiment, the DUT 1 measured while the DUT 1 stands vertically, the posture of the DUT 1 is not limited to the vertically-standing position. For example, the DUT 1 may be laid down horizontally.

The invention claimed is:

1. A fixture comprising a fixing surface in the same shape as an end surface of a device under test which is measured by irradiating an electromagnetic wave to be measured having a frequency equal to or more than 0.01 terahertz and equal to or less than 100 terahertz on the device under test, wherein:
   the end surface is fixed to the fixing surface;
   a relationship $n1-0.1 \leq n0 \leq n1+0.1$ holds, where $n0$ denotes a refractive index of the fixture and $n1$ denotes a refractive index of the device under test; and
   the fixture does not cover a side surface of the device under test,
   wherein the fixture is disposed within a container that includes at least one curved surface portion that at least partially encloses the device under test, the at least one curved surface portion being a lens for refracting the electromagnetic wave.

2. The fixture according to claim 1, wherein the fixture is rotated about a straight line orthogonal to the fixing surface as an axis.

3. The fixture according to claim 2, wherein a travel direction of the electromagnetic wave to be measured is orthogonal to the straight line.

4. The fixture according to claim 1, wherein the end surface is fixed to the fixing surface by pressing the fixing surface against the end surface.

5. The fixture according to claim 4, wherein:
   there are two of the fixtures;
   the device under test has two of the end surfaces parallel with each other; and
   the two fixtures are respectively pressed against the two end surfaces.

6. The fixture according to claim 1, wherein the end surface is fixed to the fixing surface by adhering the fixing surface to the end surface.

7. The fixture according to claim 1, wherein
   the container comprises:
   a gap portion which internally disposes at least a part of the device under test; and
   an enclosure portion which includes a first curved surface portion and a second curved surface portion, and disposes the gap portion between the first curved surface portion and the second curved surface portion, thereby enclosing the gap portion, a refractive index n2 of the enclosure portion is larger than the refractive index n1 of the device under test, and both the first curved surface portion and the second curved surface portion are convex surfaces.

8. The fixture according to claim 1, wherein the container comprises:

a gap portion which internally disposes at least a part of the device under test; and an enclosure portion which includes a first curved surface portion and a second curved surface portion, and disposes the gap portion between the first curved surface portion and the second curved surface portion, thereby enclosing the gap portion, a refractive index n2 of the enclosure portion is smaller than the refractive index n1 of the device under test, and both the first curved surface portion and the second curved surface portion are concave surfaces.

9. The fixture according to claim 7, wherein a contour of a plane shape of the gap portion of the container includes an arc.

10. The fixture according to claim 1, wherein the container comprises:

a first cover portion including a first curved surface portion which receives the electromagnetic wave to be measured, and a first concave surface portion which is closer than the first curved surface portion to the device under test, and through which the electromagnetic wave to be measured transmits, and having a refractive index of n2$a$; and a second cover portion including a second concave surface portion which receives the electromagnetic wave to be measured which has transmitted through the device under test, and a second curved surface portion which is farther than the second concave surface portion from the device under test, and through which the electromagnetic wave to be measured transmits, and having a refraction index of n2$b$, and when the refractive index of the device under test is n1, if n2$a$ is larger than n1, the first curved surface portion is a convex surface, if n2$a$ is smaller than n1, the first curved surface portion is a concave surface, if n2$b$ is larger than n1, the second curved surface portion is a convex surface, and if n2$b$ is smaller than n1, the second curved surface portion is a concave surface.

11. The fixture according to claim 10, wherein n2$a$ and n2$b$ of the container are different from each other.

12. The fixture according to claim 10, wherein a curvature radius of a plane shape of the first curved surface portion of the container and a curvature radius of a plane shape of the second curved surface portion of the container are different from each other.

13. The fixture according to claim 10, wherein contours of plane shapes of the first concave surface portion and the second concave surface portion of the container include an arc.

* * * * *